US006694161B2

United States Patent
Mehrotra

(10) Patent No.: US 6,694,161 B2
(45) Date of Patent: Feb. 17, 2004

(54) APPARATUS AND METHOD FOR MONITORING RUMEN PH

(75) Inventor: Vikram P. Mehrotra, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/125,319

(22) Filed: Apr. 18, 2002

(65) Prior Publication Data

US 2002/0156356 A1 Oct. 24, 2002

Related U.S. Application Data

(60) Provisional application No. 60/285,160, filed on Apr. 20, 2001.

(51) Int. Cl.[7] ................................................ A01B 5/00
(52) U.S. Cl. ...................................... 600/361; 600/300
(58) Field of Search ................................ 600/361, 300, 600/301, 309

(56) References Cited

U.S. PATENT DOCUMENTS

| | | | | |
|---|---|---|---|---|
| 5,984,875 A | * | 11/1999 | Brune ........................ | 600/549 |
| 6,023,630 A | * | 2/2000 | Bacchi et al. ................ | 600/348 |
| 6,241,688 B1 | * | 6/2001 | Bouda et al. ................ | 600/573 |
| 6,550,652 B2 | * | 4/2003 | Whitaker .................... | 224/191 |
| 6,582,365 B1 | * | 6/2003 | Hines et al. ................. | 600/300 |

OTHER PUBLICATIONS

Garrett, E.F.; Pereira, M.N.; Nordlund, K.V.; Armentano, L.E.; Goodger, W.J.; Oetzel, G.R., "Diagnostic Methods for the Detection of Subacute Ruminal Acidosis in Dairy Cows", *J. Dairy Science* 1999, vol. 82 (6); pp. 1170–1178.

Braun, U. Rihs, T.; Schefer, U., "Ruminal Lactic Acidosis in Sheep and Goats," *The Veterinary Record* 1992 vol. 130, No. 16: 343–349.

Dunlop, R.H., "Pathogenesis of Ruminant Lactic Acidosis," in *Advances in Veterinary Science and Comparative Medicine* vol. 16; Brandly, C.A.; Cornelius, C.E., Eds.; Academic Press, New York, 1972: pp. 259–302.

* cited by examiner

*Primary Examiner*—Max F. Hindenburg
*Assistant Examiner*—Navin Natnithithadha
(74) *Attorney, Agent, or Firm*—George R. Beck; Gary M. Bond; Howrey Simon Arnold & White, LLP

(57) ABSTRACT

The present invention provides for an apparatus and a method for monitoring, in vivo, the ruminal pH of an animal. The apparatus has an external aspect at the outside of the animal, an indwelling ruminal aspect; and an intermediate aspect between the external and indwelling aspects. The indwelling aspect further has a pH sensor; and the external aspect further having a housing and a means for storing data from the pH sensor in said housing. The apparatus may further comprise a means for transmitting signals corresponding to the pH data collected and a means for receiving said signals. The method of monitoring, in vivo, the pH of the rumen of an animal includes installing any of the embodiments of the apparatus to the animal and taking a plurality of measurements of the pH from the apparatus, and transmitting signals corresponding to said measurements to a receiving device.

21 Claims, 3 Drawing Sheets

APPARATUS AND METHOD FOR MONITORING RUMEN PH

This application claims the benefit of U.S. Provisional Application Ser. No. 60/285,160 filed Apr. 20, 2001, the entire contents of which is herein incorporated by reference.

BACKGROUND OF THE INVENTION

Although ruminal acidosis typically involves a lowering of ruminal pH to below pH 5.5 to 5.6, it is generally not adequate to define ruminal acidosis as being caused by low ruminal pH. Ruminal acidosis often occurs under intensive management. The ruminal problems are typically a result of dietary management, such as misfeeding of the ration (e.g., single large or "slug" feedings) or feeding of highly digestible carbohydrates, underfeeding of effective fiber, or all of the above. The degree of ruminal acidosis can vary from cases of indigestion with a mild scour to cases of sudden death or a very severe and distressing illness resulting in death (Braun et al., 1992). The outlook may often be poor and it may lead to complications, such as pregnancy toxemia.

Acute acidosis presents specific signs and symptoms which, if caught in time, can be treated directly. Sub-clinical acidosis, however differs in many respects from the acute form. Sub-clinical, or chronic, ruminal acidosis is best described as a syndrome related to a fermentative disorder of the rumen. Clinical symptoms of sub-clinical acidosis frequently may go undetected. Often times, sub-clinical acidosis is found in well-managed, high producing herds. Changes in an animal's ration (i.e., adequate effective fiber, altering forage: concentrate rations, feeding strategies, etc.) influence ruminal pH which can affect the occurrence of sub-clinical acidosis.

Sub-clinical acidosis is a temporarily altered rumen state which causes some aberration in patterns of fermentation and decreased in pH of the rumen, however, intensity and duration are not adequate to cause immediate overt clinical signs. Often times sub-clinical acidosis is dismissed for other problems, such as poor forage quality, poor bunk management, etc. and is not addressed. The challenge is that other disease processes also can cause symptoms listed previously.

The major clinical manifestation of sub-clinical acidosis is reduced and/or cyclic feed intake. Other associated signs include: decreased efficiency of milk production, reduced fat test, poor body condition despite adequate energy intake, high culling rate, unexplained diarrhea, and episodes of laminitis.

Although there are guidelines, high producing cows consuming large quantities of grain (55 to 60% of dry matter intake) will have a tendency toward lower ruminal pH's during the day. The critical question yet to be addressed is how low can pH go, and for how long before negative effects will be demonstrated?

There are different physiological occurrences that normally take place in a cow's transition through the lactation cycle which predispose her to higher risks of acidosis. During the transition period and through 50 days postpartum, management of the cow mediated events play an important role in the development of acidosis. Interpretation in the "normal ecological balance" within the rumen can ultimately play a role in predisposing the animal to sub-acute acidosis. When intake is reduced, energy metabolism of the rumen microorganisms as well as the host system is affected. Intake is controlled by a balance of physical mechanisms and mechanisms of the rumen environment. The challenge is to ensure that both mechanisms are working together in such a manner that one does not overpower the other (i.e., too high grain, and/or fermentable carbohydrate versus too much forage). Although there are several factors (i.e., heat, cold facilities, management, diet composition, etc.) that influence intake, managers ultimately must anticipate and compensate for intake challenges associated with normal daily practices on a given farm.

Therefore, ruminal acidosis can have a tremendous negative economic impact, such that it drains productive efficiency potential from dairy herds. The costs associated with sub-clinical ruminal acidosis are often difficult to accurately identify. Setting a confirmed cause and effect to allocate health disorders to chronic acidosis is the problem. Factors to consider include each case of digestive upset, each cow that is culled for laminitis-related lameness, reduced production because cows eat less because they have sore feet or digestive upset, reduced feed efficiency that depresses the nutrient value of feeds even though the price paid per ton remains, and similar considerations. The potential costs to the dairy industry are huge. The present methods of preventing or detecting acidosis are not optimally effective in resolving and/or managing the problem.

The only determinative diagnostic test of sub-clinical acidosis is ruminal pH. Sampling the rumen pH by stomach tubing is plagued with false interpretation because of saliva contamination. Rumen cannulation is the preferred method of obtaining representative samples of rumen fluid, although this has traditionally been used only for research purposes because of the large size of the fistula or cannula that is created and used. The installation of such a large device in the animal and the resulting impact of that installation and residency greatly reduces the economic sale value of the animal. The market value of the animal, with a large fistula in its side is drastically reduced or lost completely. Rumenocentesis or percutaneous needle aspiration as a means of collecting rumen fluid for diagnosis of sub-clinical acidosis in dairy herds has also been used but is very labor and cow-handling intensive.

What is still needed is better equipment and methods for detecting and/or monitoring ruminal pH.

SUMMARY

The present invention includes an apparatus and method to use the same. The apparatus comprises an external aspect at the outside of the animal, an indwelling ruminal aspect; and an intermediate aspect between the external and indwelling aspects. The indwelling aspect further comprises a pH sensor; and the external aspect further comprises a housing and a means for storing data from the pH sensor in said housing.

DESCRIPTION OF ILLUSTRATIVE EMBODIMENTS

Figure 1:
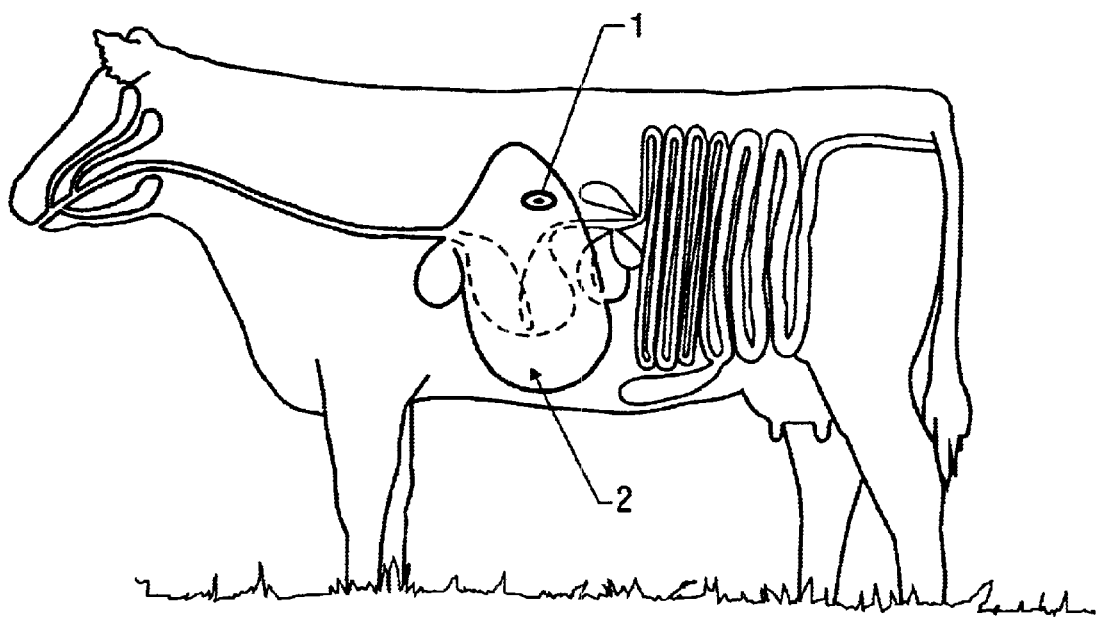
FIG. 1 is a schematic depiction of the typical placement of the apparatus in a bovine rumen. The small oval (1) indicates the point where the apparatus is attached to the cow and enters the cow's rumen (2).

In general, the invention is an apparatus for monitoring the pH in the rumen of a ruminant (preferably a bovine), the apparatus comprising a pH sensing means, suitable for being continuously situated within said rumen for at least about 48 hours, said pH sensing means being capable of measuring the pH of the rumen contents with which it is in contact and providing a signal (electronic or otherwise) representing the measured pH to the external surface of the abdominal wall of the ruminant; and a signal transmitting means, suitable for and capable of being attached to said external surface and collecting and, preferably, also storing data from said signal and/or transmitting said signal to a signal receiving station at a nearby location. Preferably, but not necessarily, the location of the receiving station is independent of the location of the ruminant.

Any suitable pH probe may be installed and used in the apparatus of the presently disclosed invention. Suitable pH probes are made by a large number of manufacturers and are well known to those of ordinary skill in the art.

In some embodiments the apparatus further comprises a cannula through which the pH sensing means can be maintained in connection with said signal transmitting means. The cannula preferably has a diameter of less than about 3 inches, more preferably the diameter is less than about 2 inches, less than about 1.5 inches, or less than about 1 inch. Most preferably the diameter of the intermediate aspect of the apparatus is less than about 0.5 inches.

In some embodiments the apparatus comprises an external aspect outside of the animal, an indwelling, ruminal, aspect; and an intermediate aspect between and connecting the external and indwelling aspects. The indwelling aspect further comprises a pH sensor; and the external aspect further comprises a housing and a means for storing data from the pH sensor in said housing. The device preferably comprises: (i) an electric clock and/or microprocessor (preferably as part of the electronic circuitry on a printed circuit board) which may be employed to receive and/or store, for later retrieval, the sensor inputs, control the frequency of data collection, and/or direct transmission of the data; (ii) a transmitter or a transceiver (preferably in the megahertz or gigahertz range), (iii) an antenna, and (iv) a switch mechanism to turn the device on and off and/or to reset it.

The data collection and transmission frequency may also be altered and controlled by the microprocessor. In a particular embodiment, the pH data can be collected every 20 to 30 minutes and stored in the memory chip. This stored information is then transmitted to a receiver every 12 hours.

In some embodiments the apparatus comprises a rumen pH sensing means, a means for producing an electronic signal of the measured pH; and a signal transmitting means, attached to the external surface, for transmitting said signal to a signal receiving station.

The transmitting means may be either "hard-wired" or wirelessly linked to a receiving station. If "hard-wired" the receiving station is preferably mounted on the animal whose ruminal pH is being monitored. The receiving station may further comprise a display means for reading the ruminal pH from a display attached to the animal.

The invention is preferably of a small size at the intermediate aspect of the apparatus and therefore, the requisite, invasive fistula that must be established in the animal's body wall, is similarly of small size. Preferably the intermediate aspect of the apparatus has a diameter of less than about 3 inches, more preferably the diameter is less than about 2 inches, less than about 1.5 inches, or less than about 1 inch. Most preferably the diameter of the intermediate aspect of the apparatus is less than about 0.5 inches.

Additionally, the external aspect of the apparatus preferably has a very low physical profile so as to prevent or minimize its getting caught or broken when the animal rubs on or brushes against something.

The method of monitoring the in vivo pH of the rumen of a ruminant comprises installing an apparatus, according to any of the embodiments of the apparatus described above, into the animal and taking a plurality of measurements of the pH using the apparatus. In some embodiments the measurements may be taken at very frequent (e.g. hourly, or even more often), less frequent (e.g. daily or twice-daily), or at custom-selected intervals, depending on the animal's condition and the management needs and decisions related thereto.

According to one embodiment of the invention the signals representing the ruminal pH are provided to a signal transmitting means and subsequently transmitted to a signal receiving station. The signal receiving station may be of any type suitable for use in the instant invention. For example the receiving station may be adapted to receive the signals during direct functional contact with the signal transmitting means (e.g., in the case of a receiving station mounted on the animal and adapted to be visually or electronically read by an attendant who approaches the animal for the purpose of taking such a reading. For example a modified PDA could be used to accept data transferred from a receiving station mounted on the animal.

Alternatively, the signal receiving station may be at a location which is independent from the movement of the ruminant (e.g., when the signal transmitting means is adapted to transmit a signal or signals, representing the pH measurements to the receiving station by means of an electronic or other signal). According to various aspects of this embodiment of the invention, the signal receiving station might be located near where the animals rest and/or forage, such as mounted on a nearby fence or pole. In contrast, depending on the type of transmitting device, the receiving station could also be at a location that is some distance from the animal(s) being monitored.

The signal receiving station may comprise a antenna functionally and may be integrated with a computer, personal computer, personal digital assistant (PDA) or any other suitable means for receiving, storing, and/or processing the signal. For example a PDA or a personal computer can be modified to act as both a receiver (e.g., using wireless internet hardware and/or software, or infrared data transmission technology) and as a data storage display device by incorporating a module (comprising an antenna or other suitable receiver mechanism, such as an infrared receiver) to collect data and display the data on the PDA. Alternatively, it is envisioned that the signal receiving station could comprise a signal relaying means for relaying the signal to another location for storage and/or analysis.

In use the apparatus may be used according to the method of the present invention. The ruminant whose ruminal pH is monitored is preferably bovine (e g, a cow). It is envisioned that apparatuses according to the instant invention could be installed in multiple cows within a single herd to serve as a means for monitoring herd response to feed regimens.

The signals provided by the individual apparatus residing with each animal could be processed both individually and collectively in order to determine herd management strategies (especially feed strategies) to prevent harmful effects resulting from acidosis and/or sub-clinical acidosis.

The signals from the animals could be collected and processed at a central location (including, but not limited to, a work station or personal computer). By way of non-limiting example, a cow's ruminal pH data may be compared to data or events historical to the individual animal or to like animals and if the measured or recorded conditions or events are acceptably close to the reference data information the cow would be considered to be suffering from acidosis or sub-clinical acidosis.

It is envisioned that the referenced data may be based on either data collected from the same animal or it may be based on data collected by monitoring a plurality of animals plotting ranges and/or threshold limits for the values deemed to indicate that the animal is suffering from acidosis or sub-clinical acidosis.

To install the apparatus for use in a cow, for example, a rumen fistula may be created by inserting a commercial trocar that is used to treat bloated animals. Preferably, a cannula is then screwed through the body cavity and tightly holds the rumen epithelium to the interior body cavity wall for healing.

Preferably, the cow will have been fed within two hours before the procedure to ensure the rumen is fully distended to the body cavity. The cow should be properly restrained preferably in a cattle chute and/or anesthetized. The cannula is typically placed in the paralumbar fossa on the left side of the animal (see, e g FIG. 1). The site (usually a 10" by 10" area) for the cannula should be prepared by clipping the hair and cleaning with alcohol or other suitable disinfectant. A local anesthetic (e g, lidocaine) may be administered at the site prior to inserting the trocar. The hide of the cow may preferably be opened using a scalpel, prior to inserting the trocar. At this site, the trocar is passed through the body cavity and rumen in a downward and forward motion.

When properly installed, the apparatus should be flush against the cow's hide, furthermore, the rumen epithelium should be held tightly to the interior body cavity wall for proper healing. A rubber stopper may be temporarily placed in the lumen of the cannula to prevent any rumen fluid from leaking out of the cannula.

The cannula should be monitored for proper healing for a few days. The area around the cannula should be cleaned and dressed, as needed.

Preferably, after monitoring the cannula for at least two days, the pH device may be installed in the cannula. To install the apparatus in the cannula, remove rubber stopper from the cannula and clear the passage of the cannula. Next connect the apparatus to the cannula. The device may then be secured to the hide of the cow by any suitable means (e.g., surgical glue, suture) in multiple locations, as necessary.

The pH sensing means includes optional tubing, typically about 18 inches, that contains the glass pH probe and is introduced into the rumen through the cannula. The pH probe may then be connected to the external aspect of the apparatus and any electronic connections may also be established. The apparatus may then activated or switched on, if necessary. The housing, in this embodiment of the invention is a disk-shaped cover which may be secured to the device and in place on the animal.

With reference to the collection of data from the pH monitoring apparatus, optionally software to collect a pH measurement once every 10 seconds, or any other acceptable frequency, may be added to the apparatus or used in conjunction with the apparatus. Suitable software may be purchased or programmed, as is well known to one of ordinary skilled in the art. The apparatus may store the collected data for intermittent transmission (e g., data collected every 30 minutes and transmitted every 12 hours) or the data may be transmitted immediately after being collected (i e, data measured each 30 minutes and immediately transmitted). The data may be optionally stored and downloaded periodically to a diskette, or other suitable data storage medium, or alternatively, the data could be stored until the apparatus is queried by a receiving device (for example the apparatus could transmit the data in response to a signal, electronic or otherwise) from a computer or PDA.

In addition, the apparatus may comprise a receiver (which could also be a transceiver) with an antenna, to receive the information that the apparatus' transmitter transmits. The receiver system is preferably external to the apparatus and may be generally located such that the animals carrying the apparatuses are within about 30 to 50 feet distance (however, technology which allows this distance to be significantly greater, may also be employed). Data received may be manipulated and displayed on a computer (that may be either hardwired, wirelessly linked, or linked by modem, or other internet connection to the receiver) or other appropriate device (e g personal computer or PDA).

In various embodiments the apparatus may optionally and desirably include a power source, such as a long-life battery, solar cell or battery, methane-powered battery, rechargeable battery or suitable power source.

In various embodiments the transmissions may be either passive, active, or on demand such as when queried by an electronic device. Examples include mobile devices such as a handheld phones or PDA's (furthermore the PDA can serve as both receiver and computer for viewing and/or analyzing the data) or stationary devices mounted on a fence, pole, in a milking parlor the animal visits, or other appropriate location.

In preferred embodiments the housing and any extension or antenna has an essentially smooth and half dome-shaped outside surface that is comparatively close to the cow's body. Those skilled in the art will appreciate that the housing may also have an outside surface that is dimpled, ridged, spongy or otherwise having texture or relief thereon and still be within the scope of the invention as claimed herein.

It is to be further understood that the specific embodiments of the present invention as set forth are not intended as being exhaustive or limiting of the invention, and that many alternatives, modifications, and variations will be apparent to those of ordinary skill in the art in light of the foregoing description. Accordingly, this invention is intended to embrace all such alternatives, modifications, and variations that fall within the scope of the claims.

The following example(s) are included to demonstrate application of the invention, and as such are not intended to be limiting. It should be appreciated by those of skill in the art that the techniques disclosed in the example(s) which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1
Evaluation of a Rumen pH Probe in a Non-Lactating Cow

1.1 Summary

A prototype pH sensor was placed in the rumen of a non-lactating Holstein cow (through a rumen cannula) to: (i) compare ruminal pH measured by a pH sensor in a rumen with fluid collected from the rumen that was measured with a calibrated pH meter, and (ii) compare ruminal pH (measured with a calibrated pH meter) from different locations in the rumen. The average ruminal pH measured by the prototype pH sensor (6.54) was similar to the average pH of the ruminal fluid (6.55) as measured by the calibrated pH meter. Ruminal pH as measured by the prototype sensor or calibrated pH meter was also similar over time. The average ruminal pH measured at the sensor location, reticulum, top, center, and bottom of the rumen, and by the prototype sensor was 6.47, 6.72, 6.40, 6.49, 6.57, and 6.60, respectively. The pH measured by the prototype was slightly higher than the pH meter at the sensor location and similar to the bottom of the rumen.

1.2 Test Subject, Conditions, and Equipment

The study was conducted on a non-lactating Holstein cow fitted with a 4-inch ruminal cannula.

Figure 2:
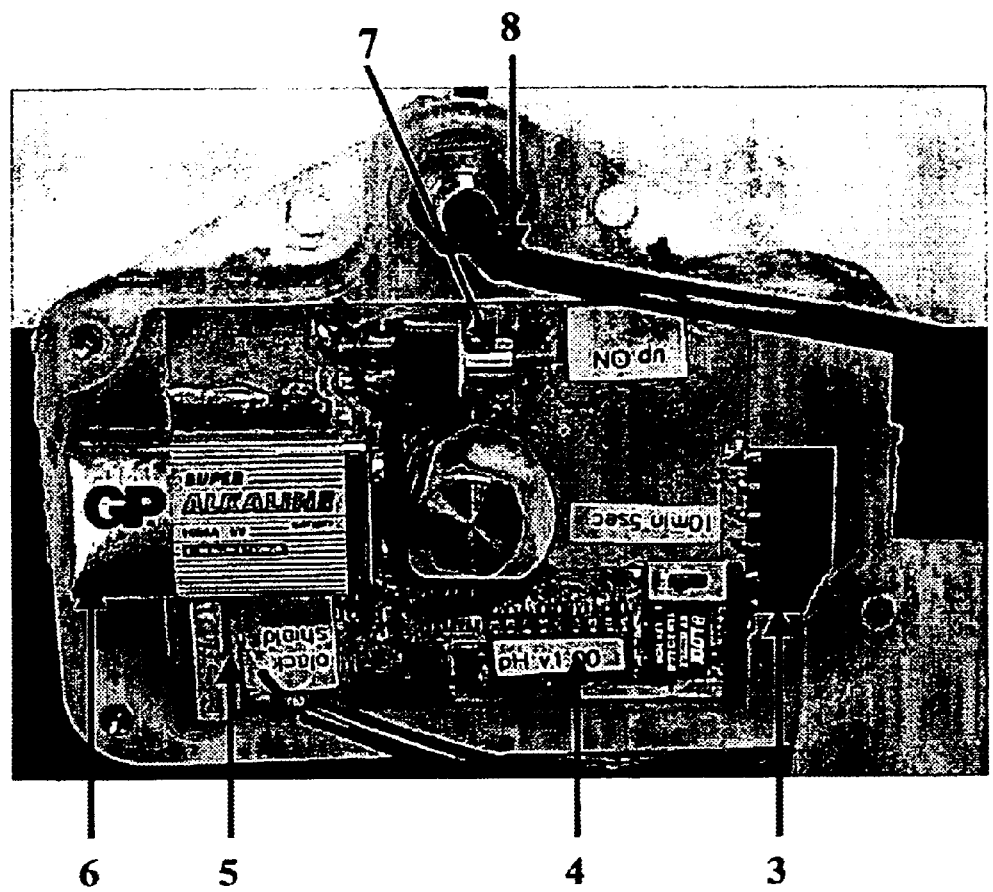
FIG. 2 is a photo of the prototype device, which indicates the location of the transmitting antenna (3), the electronic transmitter/microprocessor (4), the pH probe connections (5), the battery (6), the power switch (7), and the lead to the pH probe (8).

The prototype pH sensor comprised a glass electrode attached via electrical lead to a box containing the electronic components. The device (FIG. 2) was affixed to the rumen cannula and the glass electrode was inserted into the rumen through a hole in the cannula. A laptop computer containing an antenna was used to collect the pH data electronically from the pH sensor. The laptop computer was placed on a table adjacent to the pen where the cow was kept.

The subject-cow was housed in a box stall by itself. The cow was fed twice daily at 0730 and 1500 hours. The lights in the building remained on from 0730 to 1700 hours. The cow was fed a total mixed ration containing 60% chopped hay and 40% grain on an as-fed basis.

The prototype pH sensor was inserted into the rumen on day 0 of the study. Ruminal pH data from the pH sensor was collected electronically as programmed by the current control system (every 10 seconds) for the duration of the study.

1.2.1 Collection and pH Measurement of Ruminal Fluid

After the prototype pH sensor had been in place, in the rumen, for at least two hours, an intense ruminal fluid collection period occurred for on day. Ruminal fluid was collected every 20 minutes beginning four hours before the 1500 hour feeding and continuing for four hours after the 1500 hour feeding (1100 to 1900 hours).

During the ruminal fluid collection period, a pH measurement, from the prototype pH sensor, was collected by telemetry and recorded. Immediately after this event, the cannula stopper was removed and ruminal fluid was collected by inserting a ruminal fluid collection tube through the rumen mat to the ventral rumen (this procedure was carried out so as to minimize the disturbance at the location of the prototype pH sensor). Once the collection tube was inserted, vacuum was applied to the collection tube and the tube was moved up-and-down through the fluid and mat phases of the rumen until at least 250 ml of ruminal fluid was collected. The ruminal fluid was then removed and the cannula stopper replaced. The ruminal fluid was then transferred to a beaker for measurement of pH using a calibrated pH meter (specifically a Model 8000 pH meter from VWR Scientific Products with a Beckman Coulter 3-in-1 pH electrode with ATC Probe Cat. No. BK511052). The pH measurement was recorded on a data form.

1.2.2 Ruminal Fluid pH from Different Locations in the Rumen

On day 0 of the study, ruminal fluid pH was measured directly by placing the calibrated pH meter in five locations in the rumen, namely: (i) TOP—dorsal sac of the rumen at the opening of the fistula, (ii) CENTER—center of the rumen, (iii) BOTTOM—ventral sac of the rumen below the opening of the fistula, (iv) RETICULUM, and (v) SENSOR—at the same site as the prototype pH sensor. Rumen fluid pH was measured every 30 minutes starting 2 hours before the 1500 hour feeding and continuing until 2.5 hours after the 1500 hour feeding (1300 to 1730 hours).

To directly measure ruminal pH, the cannula stopper was removed and the probe from the calibrated pH meter was first inserted, by hand, into the rumen to the site of the flexible prototype pH sensor. A pH measurement from the prototype pH sensor was collected electronically and recorded on the data form and then the pH measurement from the calibrated pH meter was read and recorded. The calibrated pH meter probe was then moved immediately to the TOP, CENTER, BOTTOM, and RETICULUM (in that order) for sequential measurement and recordation of the pH at these locations. The cannula stopper was then inserted until the next measurement.

1.2.3 Feed Intake

The cow was fed a restricted amount of feed (12 lbs. per day as fed) and was given a limited period of time in which to consume the feed. The amount of feed given was recorded as was the amount of feed remaining after the limited feed period. Records were also kept regarding when the cow was fed and when the remaining feed was removed.

1.3 Results and Discussion

Figure 3:
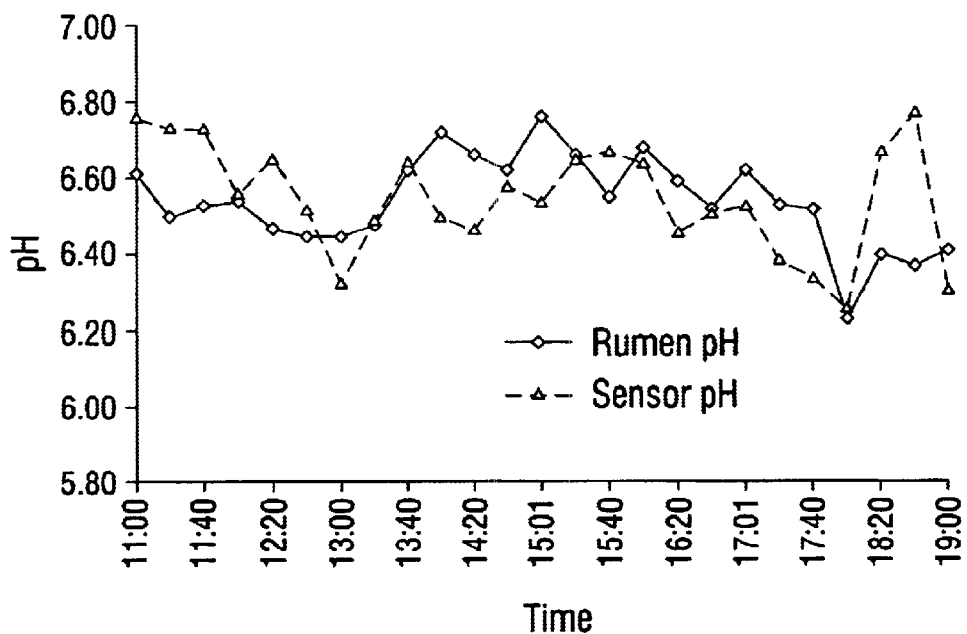
FIG. 3 shows a comparison of ruminal pH measured by either a calibrated pH meter or the prototype sensor as measured over time.

1.3.1 Comparison of pH Measured by Calibrated pH Meter and Prototype pH Sensor Ruminal pH measured by the prototype pH sensor was similar to the pH of ruminal fluid as measured by the calibrated pH meter. Ruminal fluid pH as measured by the calibrated pH meter averaged 6.54±0.12 and the pH measured by the prototype pH sensor averaged 6.55±0.15 for the 25 measurements taken during the study. Ruminal pH measured by the calibrated pH meter and prototype pH sensor was similar over time (the greatest difference observed between the two devices was 0.4 pH units) (FIG. 3).

1.3.2 Measurement of Ruminal pH in Multiple Locations in the Rumen

Figure 4:
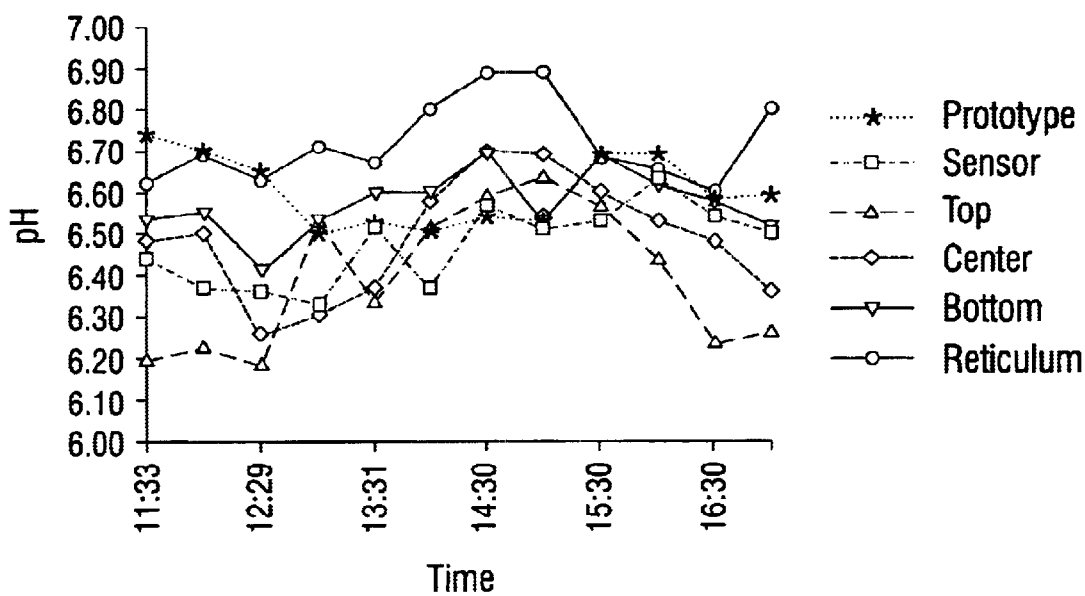
FIG. 4 shows a comparison of ruminal pH measured in various locations of the rumen over time.

Ruminal pH was the highest in the reticulum (6.72±0.10). Ruminal pH was the lowest at the TOP of the ruminal mat (6.4±0.17) and increased as pH was measured in the CENTER (6.49±0.14) and BOTTOM of the rumen (6.57±0.08). Ruminal pH at the sensor (6.47±0.10) was similar to the CENTER location since the sensor was located in the center of the rumen. However, the pH measured by the prototype (average=6.60±0.10 was most similar to the BOTTOM of the rumen as measured by the calibrated pH meter. Ruminal pH for the different locations was plotted in (FIG. 4). These data suggest that the pH measured by the prototype was slightly higher than the pH measured, at the sensor location, by the calibrated pH meter. However, a plot of the pH measurement by the prototype and at different locations in the rumen had a similar shaped curve over time (FIG. 4).

1.4 Conclusion

The prototype pH sensor was located in the ruminal mat. The pH measured by the prototype sensor was slightly higher than the pH measured by the calibrated pH meter at the sensor location and similar to the pH measured at the bottom of the rumen.

Ruminal pH measured by the prototype pH sensor was similar to the pH of ruminal fluid collected from the rumen and measured by the calibrated pH meter. The plot of pH measurements taken over time had a similar shaped curve for the pH sensor and pH from ruminal fluid and pH at different locations in the rumen.

What is claimed is:

1. An apparatus capable of monitoring the ruminal pH of a ruminant comprising:

(a) a pH sensing means, which measures pH, functionally connected to (b) a means for producing a signal, corresponding to a measured pH; and (c) a signal collection and storage means;

(d) a signal transmitting means (e) a cannula, wherein said apparatus is capable of being affixed to the ruminant and taking a plurality of ruminal pH measurements.

2. The apparatus of claim 1 and further comprising a receiving station located outside of the ruminant and capable of receiving signals sent by the signal transmitting means.

3. The apparatus of claim 2 wherein the receiving station's location is independent of the ruminant's movement.

4. The apparatus of claim 1 comprising: (a) an aspect external to the ruminant; b) an indwelling aspect, and (c) an intermediate aspect functionally connecting the external and indwelling aspects.

5. The apparatus of claim 4 wherein the apparatus is capable of being fixedly attached externally to the ruminant.

6. The apparatus of claim 5 wherein the indwelling aspect comprises the pH sensing means and wherein the external aspect further comprises a housing attached to and protecting the:

(i) signal collection and storage means and/or (ii) signal transmitting means.

7. The apparatus of claim 1 wherein the cannula is less than about 3 inches in diameter.

8. The apparatus of claim 1 wherein the pH sensing means is capable of being maintained continuously within the rumen for at least 48 hours.

9. The apparatus of claim 8 wherein the signal transmitting means is capable of transmitting the signal to a location independent of the movement of the ruminant.

10. The apparatus of claim 1 wherein the ruminant is a bovine.

11. A method for monitoring the ruminal pH of a ruminant, comprising:

(a) providing a pH sensing means to the rumen of the ruminant through a cannula;

(b) measuring the pH of the rumen;

(c) generating a signal representing the ruminal pH; and (d) providing said signal to:

(i) a signal collection and storage means, or (ii) a signal transmitting means.

12. The method of claim wherein the ruminant is bovine.

13. The method of claim 11 comprising fixedly attaching to the ruminant an apparatus comprising:

(a) a pH sensing means, which measures pH, functionally connected to (b) a means for producing a signal, corresponding to a measured pH; and (c) signal collection and storage means;

(d) signal transmitting and (e) a cannula capable of providing an avenue through which the pH sensing means can be maintained in functional contact with the signal collection and storage means, the signal transmitting means, or both.

14. The method of claim 13 wherein the apparatus comprises an aspect external to the ruminant; an indwelling aspect, and an intermediate aspect functionally connecting the external and indwelling aspects.

15. The method of claim the apparatus is fixedly attached externally to the ruminant.

16. The method of claim 14 wherein the indwelling aspect of the apparatus comprises the pH sensing means and wherein the external aspect of the apparatus further comprises a housing attached to and protecting the:

(i) signal collection and storage means and/or (ii) signal transmitting means.

17. The method of claim 11 wherein the cannula is less than about 3 inches in diameter.

18. The method of claim 13 wherein the pH sensing means is capable of being continuously maintained in the rumen for at least 48 hours.

19. The method of claim 11 comprising providing said signal to a signal transmitting means and further comprising transmitting said signal to a receiving station.

20. The method of claim wherein said receiving station is:

(a) adapted to receive said signal during functional contact with said signal transmitting means, or (b) in a location which is independent of the movement of the ruminant.

21. The method of claim wherein the receiving station comprises a computer or a personal digital assistant (PDA).

* * * * *

UNITED STATES PATENT AND TRADEMARK OFFICE
CERTIFICATE OF CORRECTION

PATENT NO. : 6,694,161 B2
DATED : February 17, 2004
INVENTOR(S) : Vikram P. Mehrotra It is certified that error appears in the above-identified patent and that said Letters Patent is hereby corrected as shown below:

Column 9,
Line 11, delete "and".
Line 13, after "means", insert -- ; and --.
Line 19, before "further", delete "and".
Line 41, delete "8", insert -- 1 --.

Column 10,
Line 6, after "claim", insert -- 11 --.
Line 25, after "claim", insert -- 14 --.
Line 41, after "claim", insert -- 19 --.
Line 47, after "claim", insert -- 20 --.

Signed and Sealed this

Third Day of August, 2004

JON W. DUDAS
*Acting Director of the United States Patent and Trademark Office*